(12) United States Patent
Mascarenhas (10) Patent No.: US 10,369,191 B2
(45) Date of Patent: Aug. 6, 2019

(54) MODULATION OF EPIGENETIC STRESS RESPONSE

(71) Applicant: Desmond D. Mascarenhas, Auburn, CA (US)

(72) Inventor: Desmond D. Mascarenhas, Auburn, CA (US)

( * ) Notice: Subject to any disclaimer, the term of this patent is extended or adjusted under 35 U.S.C. 154(b) by 0 days.

(21) Appl. No.: 15/268,079

(22) Filed: Sep. 16, 2016

(65) Prior Publication Data

US 2018/0078608 A1 Mar. 22, 2018
US 2018/0185442 A9 Jul. 5, 2018

Related U.S. Application Data

(63) Continuation-in-part of application No. 14/667,241, filed on Mar. 24, 2015, now abandoned.

(51) Int. Cl.
*A61K 38/17* (2006.01)
*G01N 33/68* (2006.01)

(52) U.S. Cl.
CPC .......... *A61K 38/17* (2013.01); *G01N 33/6893* (2013.01); *G01N 2800/52* (2013.01)

(58) Field of Classification Search
CPC ... A61K 38/17; C12Q 1/6883; G01N 33/6893
See application file for complete search history.

(56) References Cited

U.S. PATENT DOCUMENTS

2011/0212079 A1\* 9/2011 Mascarenhas ..... A61K 31/7088
424/130.1

OTHER PUBLICATIONS

Mascarenhas et al., (Int. J. Burn Trauma. Nov. 2013. 3(4):190-200) (Year: 2013).\*

\* cited by examiner

*Primary Examiner* — Michael D Pak (57) ABSTRACT

Stress, such as from physical, metabolic or psychological trauma, is associated with enduring secondary complications leading to morbidity and/or death in subjects that receive the stress insult. The epigenetic oxidative stress response to a stress insult is characterized by (a) global epigenetic events such as changes in DNA methylation and phosphorylation of Ser10 and acetylation of Lys9/14 residues of histone-3 (b) significant systemic elevations in analytes of oxidative stress in body fluids such as blood or urine and (c) deterioration of clinically relevant parameters such as glycemic control, organ function, lean body mass and rate of healing. The applicant teaches a method of counteracting the grave systemic effects of stress insult with reference to the epigenetic oxidative stress response, by daily subcutaneous bolus injections of nephrilin peptide beginning soon after insult and continuing for seven days. These methods of combating epigenetic oxidative stress response are new and have not been described in the prior art. Specifically, the use of nephrilin (acting on its target, Rictor complex) to obviate the epigenetic changes in trauma that result in systemic oxidative stress, is new. Previously disclosed work on nephrilin had not described its effects on epigenetic change (mechanism) or oxidative stress (readout). The relevance of this particular epigenetic-oxidative-stress cascade to clinically relevant outcomes such as loss of organ function, glycemic control or lean body mass was unknown, as was the use of nephrilin molecule to counteract these phenomena. The invention relates to the use of specific therapeutic agents such as nephrilin to ameliorate the epigenetic oxidative stress response, and specifically the above-mentioned clinically relevant parameters.

11 Claims, 5 Drawing Sheets

Specification includes a Sequence Listing.

SEQUENCE LISTING

```
<160> NUMBER OF SEQ ID NOS: 3

<210> SEQ ID NO 1
<211> LENGTH: 40
<212> TYPE: PRT
<213> ORGANISM: Artificial sequence
<220> FEATURE:
<223> OTHER INFORMATION: synthetic

<400> SEQUENCE: 1

Arg Gly Val Thr Glu Asp Tyr Leu Arg Leu Glu Thr Leu Val Gln Lys
1               5                   10                  15

Val Val Ser Lys Gly Phe Tyr Lys Lys Lys Gln Cys Arg Pro Ser Lys
            20                  25                  30

Gly Arg Lys Arg Gly Phe Cys Trp
        35                  40

<210> SEQ ID NO 2
<211> LENGTH: 53
```

```
<212> TYPE: PRT
<213> ORGANISM: Artificial sequence
<220> FEATURE:
<223> OTHER INFORMATION: Synthetic

<400> SEQUENCE: 2

Ala Cys Arg Leu Tyr Ala Thr Lys His Leu Arg Val Leu Leu Arg Ala
1               5                   10                  15

Asn Val Glu Phe Phe Asn Asn Trp Gly Ile Glu Leu Leu Val Thr Gln
            20                  25                  30

Leu His Asp Lys Asn Lys Thr Ile Ser Ser Glu Ala Leu Asp Ile Leu
            35                  40                  45

Asp Glu Ala Cys Glu
            50

<210> SEQ ID NO 3
<211> LENGTH: 30
<212> TYPE: PRT
<213> ORGANISM: Artificial sequence
<220> FEATURE:
<223> OTHER INFORMATION: Synthetic

<400> SEQUENCE: 3

His Glu Ser Arg Gly Val Thr Glu Asp Tyr Leu Arg Leu Glu Thr Leu
1               5                   10                  15

Val Gln Lys Val Val Ser Pro Tyr Leu Gly Thr Tyr Gly Leu
            20                  25                  30
```

MODULATION OF EPIGENETIC STRESS RESPONSE

CROSS REFERENCE

This application claims priority to and is a continuation in part of, U.S. non-provisional patent application Ser. No. 14/667,241 filed on Mar. 24, 2015, which claims priority to U.S. Provisional Patent Application Ser. No. 61/970,241 filed on Mar. 25, 2014, both of which are incorporated by reference herein in their entirety.

TECHNICAL FIELD

The invention relates to the field of medical diagnostics and therapeutics, and more particularly to methods for recognizing and treating biological phenomena that significantly exacerbate disease via epigenetic responses to stress, and for identifying molecules that may be selectively active on epigenetic changes associated with human genetics, stress, environmental influences and disease. In particular, this invention relates to epigenetic changes associated with mitochondrial dysfunction. The invention also relates to specific therapeutic agents that regulate the binding of Rictor to its binding partners, thereby affecting the epigenetic complications of stress-related processes.

BACKGROUND

Traumatic stress, such as from physical trauma, open-heart surgery or severe burns, is associated with secondary complications leading to morbidity and death in subjects that receive the traumatic insult. The mechanisms by which such serious consequences develop in a subset of the population are incompletely understood but are believed to involve neuroimmunological processes that may, for example, result in altered responses to infection, leading to sepsis and organ failure. In the intensive care unit (ICU) trauma and sepsis are leading causes of mortality. The rate of this type of ICU mortality has remained largely unchanged for several decades and new approaches for early detection of at-risk individuals and effective interventions that reduce the immunosuppressive effects of stress, organ failure and death are desperately needed.

A neuroimmunological stress response (NSR) caused by a traumatic, xenobiotic, oxidative, nociceptive or physiological stressor is often characterized by the release of peptides such as Substance P or calcitonin-related peptide (CGRP) from sensory nerves into the tissues and the triggering of complex downstream events such as acute inflammation and apoptotic cell death (in the shock phase) followed by a persistent stage of mitochondrial dysfunction and bioenergetic failure characterized by loss of tissue ATP, immunosuppression, sepsis, hypermetabolism, peripheral insulin resistance, overproduction of reactive oxygen species, impaired wound healing and chronic pain, among other complications. This phase may sometimes result in multiple organ failure and death of the patient. No fully effective intervention for these complications of stress and trauma has been developed to date.

Persistent dysfunction consequent to stress or trauma may be associated with changes in cellular chromatin (epigenetic remodeling). Among the best-understood types of epigenetic reprogramming include histone modifications and DNA methylation, especially in the promoter regions of genes. Epigenetic modification offers mammalian cells a powerful strategy for rapid, large-scale adjustment of transcriptional and post-transcriptional mechanisms in response to changing environmental challenges.

Epigenetic remodeling has been implicated in a variety of important disease and pathological processes as well as in aging. Among many examples: chronic kidney disease (Dwivedi R S et al, 2011); cancer (Choi J D and Lee J-S, 2013); alcohol exposure (Zachari S, 2013); chronic pain (Buchheit T et al, 2012); psychiatric disorders (Schmitt A et al, 2014); lupus (Hedrich C M and Tsokos G C, 2011); and aging (Cencioni C. et al, 2013).

Epigenetic switches may explain the underlying biology of many chronic pathophysiological processes. The so-called diseases of western civilization (chronic conditions such as arthritis, lupus, psoriasis, asthma, painful bladder syndrome, colitis, neuropathic pain, fibromyalgia and other immune-mediated diseases, osteoporosis, autism, atherosclerosis and other cardiovascular diseases, cancers and metastases of the breast, prostate and colon, metabolic syndrome-related conditions such as cardiovascular dysfunctions, diabetes, pulmonary arterial hypertension and polycystic ovary syndrome, nicotine- and other xenobiotic-related pathologies, neurodegenerative conditions such as Parkinson's and Alzheimer's, and ophthalmic diseases such as macular degeneration) are now increasingly viewed as associated with chronic relapsing-remitting inflammation cycles which, in turn, relate to epigenetically modified mechanisms. One common feature of nearly all of the emerging diseases in the Western world is the complexity and inter-relatedness of the underlying neuroimmunological and bioenergetic (mitochondrial) dysfunctions. Epigenetic narratives can satisfy the explanatory demands of nearly all of these complex conditions. New methodology and reagents for identifying the best points for mechanistic intervention in such putatively epigenetically controlled disease conditions is needed. Such methodology would provide a first step to the development of predictive diagnostics and adequately targeted interventions.

The inventor has recently shown that a central regulator of responses to metabolic and xenobiotic stress is the highly conserved Rictor-containing complex in mammalian cells known as mTORC2. Neurogenic inflammation pursuant to stress is associated with the release of neuropeptides such as substance P from nerve fibers in organ tissues. In kidney, a key early-warning organ, nephrilin (an inhibitor of Rictor complex) controls substance P levels in tissue following xenobiotic and traumatic stress, as well as downstream events such as macrophage activity, plasma IL-6 and TNF-alpha, tissue phosphorylation of p66shc, gene expression and other markers of oxidative damage and inflammation (Mascarenhas D et al [2012]; Mascarenhas D et al [2014]).

TOR (target of rapamycin) proteins are conserved Ser/Thr kinases found in diverse eukaryotes ranging from yeast to mammals. The TOR kinase is found in two biochemically and functionally distinct complexes, termed TORC1 and TORC2 (Rictor complex). Aided by the compound rapamycin, which specifically inhibits TORC1, the role of TORC1 in regulating translation and cellular growth has been extensively studied. mTORC2/Rictor complex is largely rapamycin insensitive and seems to function upstream of Rho GTPases to regulate the actin cytoskeleton (Jacinto E, et al [2004] *Nat Cell Biol.* 6: 1122-1128). The physiological roles of TORC2 have remained largely elusive due to the lack of pharmacological inhibitors and its genetic lethality in mammals. PRR5/PROTOR and its related family of proteins are a new class of molecules found in association to mTORC2 complex, and may be required cofactors for the function of this central regulator of neuroimmunological responses to stress. The PRR5/PROTOR gene encodes a conserved proline-rich protein predominant in kidney (Johnstone C N et al [2005] *Genomics* 85: 338-351). The PRR5/PROTOR class of proteins is believed to physically associate with mTORC2 and regulate aspects of growth factor signaling and apoptosis (Woo S Y et al [2007] *J. Biol. Chem.* 282: 25604-25612; Pearce L R et al [2007] *Biochem J.* 405: 513-522; Thedieck K et al [2007] *PLoS ONE* 2: e1217). The inventor has demonstrated the importance of a particular domain within PRR5/PROTOR comprising the sequence HESRGVTEDYLRLETLVQKVVSPYLGTYGL (SEQ ID NO:3). This sequence is conserved in human PRR5/PROTOR isoforms as well as in rat and mouse. Other obligate partners of Rictor, a central defining protein component of the mTORC2 complex, include Sin1 (also known as MIP1). Sin1 is an essential component of TORC2 but not of TORC1, and functions similarly to Rictor, the defining member of TORC2, in complex formation and kinase activity. Knockdown of Sin1 decreases Akt phosphorylation in both *Drosophila* and mammalian cells and diminishes Akt function in vivo. It also disrupts the interaction between Rictor and mTOR. Furthermore, Sin1 is required for TORC2 kinase activity in vitro (Yang Q et al [2006] *Genes Dev.* 20: 2820-2832). mTOR, SIN1 and Rictor, components of mammalian (m)TORC2/Rictor complex, are required for phosphorylation of Akt, SGK1 (serum- and glucocorticoid-induced protein kinase 1), and conventional protein kinase C (PKC). This TORC2 function is growth factor independent and conserved from yeast to mammals.

Rictor complex activity was elevated in glioma cell lines as well as in primary tumor cells as compared with normal brain tissue (Masri J et al [2007] *Cancer Res.* 67: 11712-11720). In these lines Rictor protein and mRNA levels were also elevated and correlated with increased kinase activity. Xenograft studies using these cell lines also supported a role for increased Rictor complex activity in tumorigenesis and enhanced tumor growth. These data suggest that mTORC2 is hyperactivated in gliomas and functions in promoting tumor cell proliferation and invasive potential. mTORC2 and its activation of downstream AGC kinases such as PKC-alpha, SGK1 and Akt have also been implicated in cancers of the prostate and breast (Guertin D A et al [2009] *Cancer Cell.* 15: 148-159; Sahoo S et al [2005] *Eur J Cancer.* 41: 2754-2759; Guo J, et al [2008] *Cancer Res.* 68: 8473-8481).

IRS-1 and IRS-2 are master traffic regulators in intracellular signal transduction pathways associated with growth and metabolism, playing key roles in the docking of accessory proteins to phosphorylated insulin and IGF receptors. Although similar in function, activated IRS-1 and IRS-2 proteins generate subtly different cellular outcomes, at least in part through the phosphorylation of different Akt (especially Akt 1 and Akt 2) and MAP kinase isoforms.

In diabetic humans and db/db mice the receptor for advanced glycated end products (RAGE) is activated by systemic ligands such as amphoterin, S100A9 and glycated hemoglobin (Goldin A et al [2006] *Circulation* 114: 597-605) and affects urinary albumin and/or NGAL (lipocalin-2). RAGE has been implicated in the development of kidney dysfunction consequent to elevated blood sugar (Tan A L et al [2007] *Semin. Nephrol.* 27:130-143). The inventor has recently shown that inhibition of Rictor complex and PKC reduces urinary albumin and NGAL in diabetic models (Singh B K and Mascarenhas D [2008] *Am J Nephrol* 28:890-899; Singh B K et al [2010] Metab Syn Relat Dis. 8(4): 1-10).

Variability within patient populations creates numerous problems for medical treatment. Without reliable means for determining which individuals will respond to a given treatment, physicians are forced to resort to trial and error. Because not all patients will respond to a given therapy, the trial and error approach means that some portion of the patients must suffer the side effects (as well as the economic costs) of a treatment that is not effective in that patient. It is therefore desirable to develop diagnostic methods and reagents to facilitate the identification of patients most likely to benefit from treatment for epigenetic reprogramming.

For some therapeutics targeted to specific locations within the body, screening to determine eligibility for the treatment can be performed. For example, the estrogen antagonist tamoxifen targets the estrogen receptor, so it is normal practice to only administer tamoxifen to those patients whose tumors express the estrogen receptor. Likewise, the anti-tumor agent trastuzumab (HERCEPTIN®) acts by binding to a cell surface molecule known as HER2/neu; patients with HER2/neu negative tumors are not normally eligible for treatment with trastuzumab. Methods for predicting whether a patient will respond to treatment with IGF-I/IGFBP-3 complex have also been disclosed (U.S. Pat. No. 5,824,467), as well as methods for creating predictive models of responsiveness to a particular treatment (U.S. Pat. No. 6,087,090).

The inventor has previously disclosed certain IGFBP-derived peptides known as "MBD" peptides (U.S. patent application publication nos. 2003/0059430, 2003/0161829, and 2003/0224990). These peptides have a number of properties, which are distinct from the IGF-binding properties of IGFBPs, that make them useful as therapeutic agents. MBD peptides are internalized some cells, and the peptides can be used as cell internalization signals to direct the uptake of molecules joined to the MBD peptides (such as proteins fused to the MBD peptide). Therapeutic peptides are provided by U.S. Pat. Nos. 7,618,816; 7,611,893; 7,662,624; and U.S. Patent Application Publication No. 2008/003,9393 A1; 2010.0152113 A1; the contents of each are hereby incorporated by reference is its entirety.

Combination treatments are increasingly being viewed as appropriate strategic options for designed interventions in complex disease conditions such as cancer, metabolic diseases, vascular diseases and neurodegenerative conditions. For example, the use of combination pills containing two different agents to treat the same condition (e.g. metformin plus a thiazolidinedione to treat diabetes, a statin plus a fibrate to treat hypercholesterolemia) is on the rise. It is therefore appropriate to envisage combination treatments that include moieties such as MBD in combination with other agents such as other peptides, antibodies, nucleic acids, chemotherapeutic agents and dietary supplements. Combinations may take the form of covalent extensions to the MBD peptide sequence, other types of conjugates, or co-administration of agents simultaneously or by staggering the treatments i.e. administration at alternating times.

The inventor has previously shown that MBD peptide-mediated delivery of bioactive molecules in vivo can be applied to disease processes such as cancer (Huq A, et al [2009] *Anti-Cancer Drugs* 20: 21-31) and diabetes, as described above. Nephrilin, a peptide containing the MBD scaffold, is bioactive in reducing albuminuria in diabetic mice. Nephrilin was designed to interfere with mTORC2 complex and has been shown to disrupt the association of IRS proteins with Rictor (Singh B K et al [2010] Metab Syn Relat Dis. 8(4): 1-10; U.S. Pat. No. 7,662,624). Similar approaches may be used to disrupt mTORC2 and IRS protein activity in human disease by competing the physical interaction of Rictor with obligate cofactors such as PRR5/PROTOR or Sin1/MIP1. The competing molecule may be a cell-penetrating peptide, protein, antibody or nucleic acid, or a small chemical molecule. In this work we describe in vitro assay systems that facilitate rapid screening of candidate molecules for such a purpose. Any metabolic, systemic, degenerative, or inflammatory disease process may be a candidate for interventions using such molecules.

The central role played by mTORC2 in regulating diseases of stress and aging has not been well documented. Nephrilin, an inhibitor of the binding of Rictor—the canonical component of mTORC2 complex—to its binding partners or cofactors such as PRR5/PROTOR, Sin1 and IRS proteins, is the only specific inhibitor of its class described to date. The inventor has shown that nephrilin can reverse immunological dysfunctions and disease processes relating to complications of diabetes and hypertension; acute kidney injury from rhabdomyolysis or xenotoxic stress with platinum compounds or aminoglycoside antibiotics; cancer metastasis; the neuroimmunological sequelae of burn trauma; and mortality from sepsis. These results implicate mTORC2 as a central regulator of diseases of aging. Fundamental common mechanisms suggested for the gamut of diseases of aging—the so-called diseases of western civilization—include oxidative stress [Pinton P and Rizzuto R (2008) Cell Cycle. 7(3): 304-308], loss of circadian circuitry [Uchida Y et al (2010) Biol. Pharm. Bull. 33(4) 535-544], loss of selective protein turnover mechanisms [Hussain S et al (2009) Cell Cycle 8:11, 1688-1697], and the epithelial-mesenchymal transition, EMT [Slattery C et al (2005) American Journal of Pathology, 167(2): 395-407]. The inventor has shown that biochemical signatures associated with each of these pathways can be reversed by treatment with nephrilin and has demonstrated, for the first time, that specific inhibition of mTORC2 may be the key to controlling diseases of stress and aging. Thus, therapeutic agents that disrupt binding of Rictor (the canonical component mTORC2) to its binding partners are of particular interest in the treatment of metabolic and cardiovascular diseases, especially those characterized by some underlying combination of insulin resistance, hyperglycemia, hypertension and hyperlipidemia; cancer progression and metastasis; acute kidney injury (AKI) in critical care settings, also including sepsis, systemic inflammatory conditions such as shock, post-operative stress such as after cardiopulmonary bypass or transplant, burns, pancreatitis, rhabdomyolysis, xenobiotic stresses caused by cocaine, alcohol, aminoglycoside antibiotics, antiviral compounds or platinum compounds; neurodegenerative diseases such as Parkinson's Alzheimer's, Huntington's and ALS/Lou Gehrig's disease; ototoxicities; autoimmune conditions such as lupus erythematosus and multiple sclerosis; genetic diseases such as cystinosis, Fanconi's and other conditions affecting mitochondrial respiration; pulmonary diseases, especially COPD and asthma and pulmonary arterial hypertension; migraine; ocular diseases such as cataracts and retinopathies, especially diabetic complications; and liver diseases, including chronic viral infections such as hepatitis. These disease states are now increasingly viewed as secondary to chronic inflammatory conditions that may, in turn, relate to neurogenic signaling and oxidative stress. A correlation between oxidative stress and processes of aging may explain the rising incidence of these diseases as a direct consequence of an aging population.

A key regulator of oxidative damage and aging is the adapter protein p66shc. Activation of this molecule by phosphorylation at serine 36 leads to mitochodrial translocation and increased production of free oxygen radicals. P66shc gene knockout mice live significantly longer and are protected from many of the diseases of aging listed above [Pinton P and Rizzuto R (2008) Cell Cycle. 7(3): 304-308]. The inventor has shown for the first time, that mTORC2 regulates the activation of protein kinase C beta-II (PKC-beta-II) by phosphorylation at threonine 641. PKC-beta was shown to be the activator of p66shc by phosphorylation of S36 [Pinton P, et al. (2007) Science 315: 659-663]. Nephrilin reverses both PKC-beta-II-T641 and p66shc-S36 phosphorylation events [Mascarenhas D et al, 2012].

A recently recognized histological consequence of cellular stress is the formation of microscopically visible punctate structures in or around the nuclei of stressed cells [Bart J. et al (2008) Cytometry 73A: 816-824]. The inventor has shown, in diseased hypertensive animals, the presence of such structures in kidney cells by immunohistochemical staining. The incidence of such structures is much reduced in animals treated with the mTORC2 inhibitor, nephrilin.

Epithelial cells of renal proximal tubules (PTECs) are known to be exquisitely sensitive to p66shc-mediated oxidative stress [Sun L et al (2010) Am J Physiol Renal Physiol. 299(5): F1014-F1025]. Damage to PTECs can be monitored by measuring albumin or lipocalin-2/NGAL in urine by using commercially available kits. In many of the proinflammatory disease conditions listed above, elevated levels of NGAL or albumin have been documented. This is especially true of AKI settings such as those encountered in patients with burns, hypoperfusion, pancreatitis and sepsis [Cruz D et al (2010) Intensive Care Med 36:444-451]. In AKI, moreover, a proinflammatory condition reminiscent of human systemic inflammatory states encountered in critical care settings, as enumerated above, can be generated in experimental animals by placing artificial stress on kidneys, such as in rhabdomyolysis and gentamycin models [Zager R et al (2006) Am J Physiol Renal Physiol 291:F546-F556]. The inventor has shown, for the first time, that this type of proinflammatory state can be successfully treated by an inhibitor of Rictor complex, nephrilin.

Activated NADPH oxidases (Nox) have been implicated in the generation of reactive oxygen species, thus playing a central role in oxidative stress in the tissues. A key player in the activation of Nox is Rac1/2, a central player in cellular GTP metabolism. Activated Rac1 (phosphorylated Ser71) is a subunit of active Nox. The inventor has shown that Rac1, as well as several molecules that serve as accessories to its activity (PKC, Prex1, p66shc, Pitx2, ERK1/2) are up-regulated in the tissues of burned animals. Treatment with nephrilin can reduce activation of Rac1-S71 as well as accessory molecules (activated PKCs, activated p66shc, etc.). These pathways are known to be integral to oxidative stress as well as pain in the CNS. Nephrilin treatment may abate neuropathies, migraine and other pain-related molecules and pathways in the CNS.

A key finding of the inventor that relates to the epigenetic memory caused by early chromatin-modifying events following severe burn trauma, is that treatment of burned animals beginning at 2 hours after burn and continuing until day 7 is more efficacious than treatment beginning at day 8 and continuing to Day 14. Evaluation of animals in both cases was done at Day 14. Differences were found on glycemic control, splenomegaly (anemia), oxidative metabolism, kidney function and several clinically relevant markers of metabolism and neuroimmune function, including changes in the CNS. These results support the narrative of epigenetic remodeling described above. Basal gene expression of key activators of oxidative stress such as PKC-beta2, Prex1, Bik and Pitx2 were stably modified in tissues of burned animals, as well as activation of downstream targets such as phosphorylated Rac1-Ser71 and phosphorylated p66shc-Ser36. These activations via phosphorylation were better controlled by nephrilin treatment on days 1-7 versus 8-14.

Burned animals show impaired glucose tolerance and elevated serum insulin levels after glucose challenge. The inventor has shown that these markers of dysregulated glycemic control are normalized by treatment with nephrilin on days 1-7. Nephrilin has also been shown to normalize impaired levels of insulin C-peptide in serum.

Burned animals show elevated levels of 8-isoprostane and 8-OHDG in urine at 14 days. The inventor has shown that nephrilin treatment dramatically reduces these markers of oxidative damage in the urine.

A well-known consequence of critical illness in general and burn injury in particular is persistent anemia secondary to impaired iron metabolism and erythropoiesis. These deficits lead to pronounced splenomegaly in burned subjects. The inventor has shown, in burned rats, that treatment with nephrilin can substantially reduce splenomegay in burned animals.

All references cited herein, including patent applications and publications, are incorporated by reference in their entirety.

SUMMARY OF THE INVENTION

The present invention provides methods of understanding, diagnosing and treating disease conditions in a mammal, especially dysfunctions related to epigenetic changes. The invention provides compositions of inhibitors of Rictor complex and methods for diagnostic and therapeutic uses thereof. Epigenetic stress response and conditions include but are not limited to diabetes, gastrointestinal disease, obesity, metabolic and cardiovascular diseases (especially those characterized by some underlying combination of insulin resistance, hyperglycemia, hypertension and hyperlipidemia); cancer progression and metastasis; acute kidney injury (AKI) in critical care settings, sepsis, systemic inflammatory conditions such as shock, post-operative stress such as after cardiopulmonary bypass or transplant, burns, blunt trauma, pancreatitis, rhabdomyolysis, xenobiotic stresses caused by cocaine, nicotine, alcohol, aminoglycoside antibiotics, cyclosporins, antiviral compounds or chemotherapeutic agents such as platinum compounds or doxorubicin; neuropathic pain and migraine; neurodegenerative diseases such as Parkinson's Alzheimer's, Huntington's and ALS/Lou Gehrig's disease; ototoxicities; autoimmune conditions such as lupus erythematosus, arthritis, psoriasis, colitis, painful bladder syndrome, fibromyalgia, and multiple sclerosis; genetic diseases such as cystinosis, Fanconi's and other conditions affecting mitochondrial respiration; other forms of mitochondrial dysfunction of bioenergetic failure; migraine; pulmonary diseases, especially COPD, PAH and asthma; ocular diseases such as cataracts and retinopathies, especially diabetic complications; and liver diseases, including chronic viral infections such as hepatitis.

In some aspects, the invention provides an agent capable of disrupting the physical association of Rictor protein with one of its obligate cofactors, thereby reversing the effects of an epigenetic signature. Examples of agents include but are not limited to peptides, proteins, antibodies, nucleic acid and small chemical molecules.

The terms "subject" and "individual", as used herein, refer to a vertebrate individual, including avian and mammalian individuals, and more particularly to sport animals (e.g., dogs, cats, and the like), agricultural animals (e.g., cows, horses, sheep, and the like), and primates (e.g., humans). The present invention describes a method for treating an epigenetic oxidative stress response to stress insult in a mammal, comprising administering to the mammal a therapeutically effective dose of nephrilin peptide (SEQ ID NO: 1) wherein such treatment results in (a) reduction in level of a marker of oxidative stress in blood or urine; and (b) improvement of one or more clinically relevant parameters selected from the group consisting of glycemic control, eGFR, lean body mass, fat mass or wound healing; thereby mitigating the effects of the epigenetic oxidative stress response in the mammal.

In embodiments of the invention, the therapeutic agent is capable of disrupting the physical association of Rictor protein with one of its binding partners selected from the group comprising PRR5/PROTOR, Sin1, IRS1 and IRS2, thereby reversing detrimental effects of the neuroimmunological stress response.

In embodiments of the invention, the composition can be administered via any route including but not limited to intravenous, oral, subcutaneous, intraarterial, intramuscular, intracardial, intraspinal, intrathoracic, intraperitoneal, intraventricular, sublingual, transdermal, and inhalation.

In an embodiment of the invention, nucleic acids encoding fusion proteins are used in methods of diagnosing or treating an inflammatory disease condition. Inflammatory disease conditions include but are not limited to trauma, sepsis, cancer, diabetes, cardiovascular disease, obesity, metabolic disease, neurodegenerative disease, gastrointestinal disease, autoimmune disease, rheumatological disease and infectious disease.

In another aspect the invention provides methods of diagnosing or treating an epigenetic condition comprising administering an effective amount of a polypeptide of the invention to a mammal. Neuroimmunological dysfunctions or conditions include but are not limited to psychological or psychosocial stress, trauma, sepsis, cancer, diabetes, cardiovascular disease, chronic kidney disease, acute kidney injury, retinopathy, obesity, metabolic disease, neurodegenerative disease, gastrointestinal disease, autoimmune disease, rheumatological disease, infectious disease, genetic disease, and xenotoxicity.

The compositions of the invention may be administered by means that include but are not limited to intravenous, oral, subcutaneous, intraarterial, intramuscular, intracardial, intraspinal, intrathoracic, intraperitoneal, intraventricular, sublingual, transdermal, and inhalation. In some embodiments, the composition is administered to a mammal at less than about 20 mg/kg/day.

The invention includes methods to diagnose or treat epigenetic stress response, dysfunction or condition by administering nucleic acids and/or vectors encoding polypeptides of the invention to a mammal.

In one aspect, the invention provides methods for treating an epigenetic stress response in a mammal characterized by one or more of a physiological attribute selected from the group consisting of elevated Substance P, CGRP, P53, PKC-beta, PKC-delta, CCL2, IL-6, glucose, lactate, ATP, lactate/ATP ratio (or ATP/lactate ratio), sirtuins (especially SIRT1, SIRT3 and SIRT5), markers of autophagy, p66shc, PGC1-alpha, and expression of a RAGE ligand gene (especially S100A9); said method comprising treating the mammal with a therapeutic agent that disrupts the binding of Rictor to a binding partner selected from the group consisting of PRR5/PROTOR/Protor, Sin1, IRS1 and IRS2; thereby reducing or reversing the neuroimmunological stress response in the mammal. In some embodiments, the neuroimmunological dysfunction or condition is selected from a group consisting of trauma, acute kidney injury, neurodegenerative disease, autoimmune disease, infectious disease, metabolic disease, cancer, genetic disease, and xenotoxicity.

In some aspects, the invention provides a therapeutic agent capable of disrupting the physical association of Rictor protein with one of its binding partners selected from the group consisting of PRR5/PROTOR, Sin1, IRS1 and IRS2, thereby reversing the effects of a biochemical signature characteristic of an neuroimmunological dysfunction in a mammal exhibiting a biochemical signature characterized by (a) one or more of a physiological attribute selected from the group consisting of substance P, CGRP, P53, PKC-beta, PKC-delta, CCL2, IL-6, glucose, lactate, ATP, lactate/ATP ratio (or ATP/lactate ratio), sirtuins (especially SIRT1, SIRT3 and SIRT5), markers of autophagy, p66shc, PGC1-alpha, and expression of a RAGE ligand gene (especially S100A9) in tissues, in response to traumatic, xenobiotic, metabolic or autoimmune stress; wherein the therapeutic agent disrupts the binding of Rictor to a binding partner selected from the group consisting of PRR5/PROTOR, Sin1, IRS1 and IRS2; thereby reducing or reversing the neuroimmunological dysfunction or condition. In some embodiments the agent is a peptide, a protein, an antibody, a nucleic acid, or a small chemical molecule. In some embodiments, the therapeutic agent is nephrilin or a sequence variant thereof. For example, the variant may have 80%, 90%, 95% or 99% identity to nephrilin in its effector domain.

In another aspect, the invention provides methods to use a therapeutic agent according to the invention, wherein the therapeutic agent is nephrilin or functional variants thereof. Nephrilin is a 40-amino acid peptide of the sequence RGVTEDYLRLETLVQKVVSKGFYKKKQCRPSKGRKRGFCW that has been previously described (Singh B K et al [2010] *Metab Syn Relat Dis.* 8(4): 1-10; Mascarenhas D et al [2012] *Inflamm. Res.* 61:1395-1404). A functional variant of nephrilin has one, two, three, four, five, six, seven, eight, nine, or ten amino acid substitutions of the nephrilin sequence and maintains the ability to disrupt the binding of Rictor to a binding partner. Alternatively, a functional variant of nephrilin has at least any one of 95%, 90%, 85%, 80%, or 75% sequence identity to nephrilin and maintains the ability to disrupt the binding of Rictor to a binding partner.

In yet another aspect the invention provides methods using a therapeutic agent wherein the therapeutic agent competes with PRR5/Protor or nephrilin in binding to its binding site on Rictor or subsets of that binding site. Preferably the therapeutic agent competes with binding of PRR5/Protor or nephrilin to the sequence ACRLYATKHLRVLLRANVEFFNNWGIELLVTQLHDKNKTISSEALDILDEACE or a subset thereof, which is part of the Rictor binding site. To measure binding, any of several available protocols, well known to practitioners in the art, may be used. For example, to measure the binding of nephrilin to various candidate peptides carrying subsets of the Rictor binding domain previously located by deletion mapping [Pearce L et al (2007) *Biochem J.* 405(3): 513-522] one may use the following method: Bind 100 ug of nephrilin to a Ni-NTA column (bed volume 0.2 ml) and pass candidate biotinylated agent (1-50 ug) plus 1 ug of streptavidin-HRP conjugate through the column. After washing the column with 4-5 column volumes of binding buffer (PBS), sample is eluted in 2 column volumes of PBS containing 100 mM imidazole and the eluate assayed for HRP using commerically available reagent TMB (read at 655 nm). Therapeutic agents, selected from the group consisting of a peptide, a protein, an antibody, a nucleic acid, and a small chemical molecule, may be identified using this assay, either as binding directly to nephrilin, as described above, or as competitors of binding of nephrilin to subsets of its binding site, as described above.

The invention discloses a method for treating a stress response in a mammal characterized by epigenetic changes in cellular chromatin and significant change in the quantity or activity one or more of a physiological attribute selected from the group consisting of Substance P, CGRP, P53, PKC-beta, PKC-delta, CCL2, IL-6, glucose, lactate, ATP, lactate/ATP ratio (or ATP/lactate ratio), sirtuins (especially SIRT1, SIRT3 and SIRT5), markers of autophagy, p66shc, PGC1-alpha, and expression of a RAGE ligand gene (especially S100A9); said method comprising treating the mammal with a therapeutic agent that disrupts the binding of Rictor to a binding partner selected from the group consisting of PRR5/PROTOR/Protor, Sin1, IRS1 and IRS2; thereby reducing or reversing the neuroimmunological stress response in the mammal. The physiological attribute may also be selected from the group consisting of urinary albumin, urinary lipocalin-2/NGAL, plasma TNF-alpha and tissue expression of UCHL1 gene.

The epigenetic stress response is associated with traumatic, xenobiotic, metabolic, oxidative or autoimmune stress. It may be associated with traumatic stress selected from the group consisting of blunt trauma, severe burn, surgery, sepsis, pancreatitis, rhabdomyolysis and psychological stress. It may also be associated with one or more forms of autoimmune stress selected from the group consisting of systemic lupus erythematosis, arthritis, colitis, Sjogren's syndrome, painful bladder syndrome, fibromyalgia, psoriasis, asthma and diabetes.

In another aspect the present invention describes diagnostic methods for identifying patient subsets for treatment according to the invention wherein the physiological attribute measured is selected from the group consisting of tissue Substance P, tissue CGRP, urinary lipocalin-2/NGAL, urinary albumin, salivary alpha-amylase, plasma IL-6, plasma TNF-alpha, and tissue expression of RAGE ligand gene or UCHL1 gene.

DETAILED DESCRIPTION OF THE INVENTION

The present invention provides methods for recognizing and treating biological phenomena that significantly exacerbate disease via neuroimmunological and epigenetic responses to stress and for modulating epigenetic changes that may be associated with stress-related complications of human trauma, pathophysiology and disease.

The inventor has shown here, for the first time, that treatment of severely burned rats with nephrilin protects against major epigenetic reprogramming in response to a major stress insult. Specifically, nephrilin prevents a significant stress-induced increase in Histone 3 Ser10 (H3S10) phosphorylation, an important cellular epigenetic switch with major implications for chromatin structure in meiosis. Nephrilin also upregulates the deacetylation of Histone 4 Lys16 (H4K16), a modification believed to control protective autophagy in mammalian cells. Moreover, in these animals, tissue LC3A (a marker of autophagy) is significantly upregulated by nephrilin treatment. Autophagy is particularly relevant in the context of mitochondrial dysfunction (consequent to stress), as one form of autophagy (mitophagy) is very important to the maintenance of a healthy pool of mitochondria in the cells.

Mitochondria produce the energy (especially ATP) needed for cellular life. Mitochondrial dysfunction lies at the heart of most morbidity and mortality in the ICU. Sepsis is associated with mitochondrial dysfunction. Loss of mitochondrial homeostasis leads to overproduction of dangerous oxidation products, loss of ATP levels in the tissues, excessive buildup of lactic acid and pyruvate from increased glycolysis, apoptotic cell death, and a variety of other complications. Bioenergetic failure is associated with a variety of disease and pathophysiological conditions, major organ failure, and death of the patient.

The inventor has shown here, for the first time, that epigenetic responses, changes or marks may be accompanied by changes in the enzymes capable of effecting epigenetic responses, changes or marks (epigenetic modifiers) and that administration of nephrilin to animals under stress can modulate the intracellular levels of said epigenetic modifiers, thereby influencing the epigenetic stress response. Examples of epigenetic modifiers include the sirtuins (especially SIRT1), other histone deacetylases, hMOF and other acetyl transferases, PKCs, Aurora kinase A and Aurora kinase B, MSK-1, and many other enzymes and regulator well-known from the published scientific literature.

The sirtuins are metabolic sensors that are link mitochondrial homeostasis to epigenetic programming in mammalian cells. The inventor has shown, for the first time that treatment of severely burned rats with nephrilin upregulates SIRT1, SIRT3 and SIRT5. SIRT3 and SIRT5 are major metabolic regulators of mitochondrial function, via deacetylation and desuccinylation processes, respectively. SIRT1 directly affects chromatin by deacetylating H4K16, and also deacetylates P53, a major regulator of apoptotic cell death pathways.

The PKCs beta and/or delta have been associated with activation of P53-driven apoptosis (by P53 Ser46 phosphorylation), p66shc-mediated ROS generation in mitochondria (by p66shc-Ser36 phosphorylation) and a major change to chromatin: phosphorylation of H3S10. PKCs are activated by Rictor complex. Treatment of severely burned rats with nephrilin, an inhibitor of Rictor complex, significantly reduces activation of PKCs beta/delta by phosphorylation at Ser660. In other rodent models of stress, nephrilin has shown similar effects on PKCs (Singh B K et al, 2010; Mascarenhas D. et al, 2012).

The inventor has shown here, for the first time, that severe burn stress in rodents is associated with changes in DNA methylation in the promoter region of genes important to metabolic or neuroimmunological homeostasis, and that treatment with nephrilin protects against this type of epigenetic change. For example, the methylation of CpGs in the IL21 receptor gene promoter is dramatically affected by stress. These changes can be partly or completely reversed by nephrilin treatment.

Adaptive biochemical signatures are provided by U.S. Patent Application Publications Nos: 2011/0202281 A1 and 2011/0212079 A1.

Methods of Identifying Candidates for Treatment

The invention provides methods for identifying and using candidate agents for protection against or reversal of epigenetic changes and mitochondrial dysfunction.

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one biochemical readout is measured (i.e., measured values for two or more readouts are obtained), the sample may be divided into a number of aliquots, with separate aliquots used to measure different readouts (although division of the biological sample into multiple aliquots to allow multiple determinations of the levels of the readouts in a particular sample are also contemplated). Alternately the sample (or an aliquot therefrom) may be tested to determine the levels of multiple readouts in a single reaction using an assay capable of measuring the individual levels of different readouts in a single assay, such as an array-type assay or assay utilizing multiplexed detection technology (e.g., an assay utilizing detection reagents labeled with different fluorescent dye markers).

As will be understood by those in the art, the exact identity of a reference value will depend on the tissue that is the target of treatment and the particular measuring technology used. In some embodiments, the comparison determines whether the measured value is above or below the reference value. In some embodiments, the comparison is performed by finding the "fold difference" between the reference value and the measured value (i.e., dividing the measured value by the reference value).

Although some assay formats will allow testing of biological samples without prior processing of the sample, it is expected that most biological samples will be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood.

Commonly, readouts will be measured using an affinity-based measurement technology. Affinity-based measurement technology utilizes a molecule that specifically binds to the readout protein being measured (an "affinity reagent," such as an antibody or aptamer), although other technologies, such as spectroscopy-based technologies (e.g., matrix-assisted laser desorption ionization-time of flight, or MALDI-TOF, spectroscopy) or assays measuring bioactivity (e.g., assays measuring mitogenicity of growth factors) may be used.

Affinity-based technologies include antibody-based assays (immunoassays) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection).

If immunoassay technology is employed, any immunoassay technology which can quantitatively or qualitatively measure the readout in a biological sample may be used. Suitable immunoassay technology includes radioimmunoassay, immunofluorescent assay, enzyme immunoassay, chemiluminescent assay, ELISA, immuno-PCR, and western blot assay.

Likewise, aptamer-based assays that can quantitatively or qualitatively measure the level of a relevant readout in a biological sample may be used in the methods of the invention. Generally, aptamers may be substituted for antibodies in nearly all formats of immunoassay, although aptamers allow additional assay formats (such as amplification of bound aptamers using nucleic acid amplification technology such as PCR (U.S. Pat. No. 4,683,202) or isothermal amplification with composite primers (U.S. Pat. Nos. 6,251,639 and 6,692,918).

A wide variety of affinity-based assays are known in the art. Affinity-based assays will utilize at least one epitope derived from the readout protein of interest, and many affinity-based assay formats utilize more than one epitope (e.g., two or more epitopes are involved in "sandwich" format assays; at least one epitope is used to capture the marker, and at least one different epitope is used to detect the marker).

Affinity-based assays may be in competition or direct reaction formats, utilize sandwich-type formats, and may further be heterogeneous (e.g., utilize solid supports) or homogenous (e.g., take place in a single phase) and/or utilize or immunoprecipitation. Most assays involve the use of labeled affinity reagent (e.g., antibody, polypeptide, or aptamer); the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays.

In a heterogeneous format, the assay utilizes two phases (typically aqueous liquid and solid). Typically readout protein-specific affinity reagent is bound to a solid support to facilitate separation of the readout indicator protein from the bulk of the biological sample. After reaction for a time sufficient to allow for formation of affinity reagent/readout indicator protein complexes, the solid support containing the antibody is typically washed prior to detection of bound polypeptides. The affinity reagent in the assay for measurement of readout proteins may be provided on a support (e.g., solid or semi-solid); alternatively, the polypeptides in the sample can be immobilized on a support. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, and Protein A beads. Both standard and competitive formats for these assays are known in the art.

Array-type heterogeneous assays are suitable for measuring levels of readout proteins when the methods of the invention are practiced utilizing multiple readout proteins. Array-type assays used in the practice of the methods of the invention will commonly utilize a solid substrate with two or more capture reagents specific for different readout proteins bound to the substrate a predetermined pattern (e.g., a grid). The biological sample is applied to the substrate and readout proteins in the sample are bound by the capture reagents. After removal of the sample (and appropriate washing), the bound readout proteins are detected using a mixture of appropriate detection reagents that specifically bind the various readout proteins. Binding of the detection reagent is commonly accomplished using a visual system, such as a fluorescent dye-based system. Because the capture reagents are arranged on the substrate in a predetermined pattern, array-type assays provide the advantage of detection of multiple readout proteins without the need for a multiplexed detection system.

In a homogeneous format the assay takes place in single phase (e.g., aqueous liquid phase). Typically, the biological sample is incubated with an affinity reagent specific for the readout protein in solution. For example, it may be under conditions that will precipitate any affinity reagent/antibody complexes that are formed. Both standard and competitive formats for these assays are known in the art.

In a standard (direct reaction) format, the level of readout protein/affinity reagent complex is directly monitored. This may be accomplished by, for example, determining the amount of a labeled detection reagent that forms is bound to readout protein/affinity reagent complexes. In a competitive format, the amount of readout protein in the sample is deduced by monitoring the competitive effect on the binding of a known amount of labeled readout protein (or other competing ligand) in the complex. Amounts of binding or complex formation can be determined either qualitatively or quantitatively.

Complexes formed comprising readout protein and an affinity reagent are detected by any of a number of known techniques known in the art, depending on the format of the assay and the preference of the user. For example, unlabelled affinity reagents may be detected with DNA amplification technology (e.g., for aptamers and DNA-labeled antibodies) or labeled "secondary" antibodieswhich bind the affinity reagent. Alternately, the affinity reagent may be labeled, and the amount of complex may be determined directly (as for dye- (fluorescent or visible), bead-, or enzyme-labeled affinity reagent) or indirectly (as for affinity reagents "tagged" with biotin, expression tags, and the like).

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one readout protein is measured, the biological sample may be divided into a number of aliquots, with separate aliquots used to measure different readout proteins (although division of the biological sample into multiple aliquots to allow multiple determinations of the levels of the readout protein in a particular sample are also contemplated). Alternately the biological sample (or an aliquot therefrom) may be tested to determine the levels of multiple readout proteins in a single reaction using an assay capable of measuring the individual levels of different readout proteins in a single assay, such as an array-type assay or assay utilizing multiplexed detection technology (e.g., an assay utilizing detection reagents labeled with different fluorescent dye markers).

It is common in the art to perform 'replicate' measurements when measuring readout proteins. Replicate measurements are ordinarily obtained by splitting a sample into multiple aliquots, and separately measuring the readout protein (s) in separate reactions of the same assay system. Replicate measurements are not necessary to the methods of the invention, but many embodiments of the invention will utilize replicate testing, particularly duplicate and triplicate testing.

In some aspects of the invention, the following readout proteins or markers include, but are not limited to: S100A9 (S100 calcium binding protein A9 [*Homo sapiens*] NM_002965.3), IRS-1 (insulin receptor substrate-1; IRS-1 [*Homo sapiens*] gi|386257|gb|AAB27175.1), IRS-2 (insulin receptor substrate-2 [*Homo sapiens*] gi|18652857|dbj|BAB84688.1), mTORC1 and mTORC2 complexes which are traditionally defined by the protein components Raptor and Rictor respectively, Rictor (RICTOR protein [*Homo sapiens*] gi|30704352|gb|AAH51729.1), mTORC2, Raptor (raptor [*Homo sapiens*] gi|21979456|gb|AAM09075.1), mTORC1; AKT SUB-FAMILY OF AGC KINASES: AKT1 protein [*Homo sapiens*] gi|18027298|gb|AAL55732.1, AKT2 protein [*Homo sapiens*] gi|111309392|gb|AAI20996.1, AKT3 protein [*Homo sapiens*] gi|62089468|gb|AAH20479.1 (NOTE:AKT is also known as Protein Kinase B, or PKB); SGK SUB-FAMILY OF AGC KINASES: SGK1 Serum/glucocorticoid regulated kinase 1 [*Homo sapiens*] gi|12654839|gb|AAH01263.1, SGK2 protein [*Homo sapiens*] gi|41351348|gb|AAH65511.1, SGK3 Serum/glucocorticoid regulated kinase 3 [*Homo sapiens*] i|15929810|gb|AAH15326.1; PKC SUB-FAMILY OF AGC KINASES: PKC-alpha; Protein kinase C, alpha [*Homo sapiens*] gi|80479084|gb|AAI09275.1, PKC-beta; Protein kinase C, beta [*Homo sapiens*] gi|22209072|gb|AAH36472.1, PKC-beta; protein kinase C, beta isoform 1 [*Homo sapiens*] gi|47157322|ref|NP_997700.1, PKC-beta; protein kinase C, beta isoform 2 [*Homo sapiens*] gi|20127450|ref|NP_002729.2, PKC-delta; protein kinase C, delta [*Homo sapiens*] gi|47157325|ref|NP_997704.1, PKC-gamma; Protein kinase C, gamma [*Homo sapiens*] gi|28839171|gb|AAH47876.1, PKC-zeta 1; protein kinase C, zeta isoform 1 [*Homo sapiens*] gi|52486327|ref|NP_002735.3, PKC-zeta 2; protein kinase C, zeta isoform 2 [*Homo sapiens*] gi|75709226|ref|NP_001028753.1, PKC-epsilon; protein kinase C, epsilon [*Homo sapiens*] gi|4885563|ref|NP_005391.1, PKC-theta; protein kinase C, theta [*Homo sapiens*] gi|5453976|ref|NP_006248.1, PKC-iota; *Homo sapiens* protein kinase C, iota gb|NM_002740. In some aspects of the invention, the readout proteins or markers are from a non-human mammal.

Kits for Identification of Candidates for MBD Peptide Therapy

The invention provides kits for carrying out the methods of the invention. Kits of the invention comprise at least one probe specific for a readout gene (and/or at least one affinity reagent specific for an readout protein) and instructions for carrying out a method of the invention. More commonly, kits of the invention comprise at least two different readout gene probes (or at least two affinity reagents specific for readout proteins), where each probe/reagent is specific for a different readout gene.

Kits comprising a single probe for a readout gene (or affinity reagent specific for a readout protein) will generally have the probe/reagent enclosed in a container (e.g., a vial, ampoule, or other suitable storage container), although kits including the probe/reagent bound to a substrate (e.g., an inner surface of an assay reaction vessel) are also contemplated. Likewise, kits including more than one probe/reagent may also have the probes/reagents in containers (separately or in a mixture) or may have the probes/affinity reagents bound to a substrate (e.g., such as an array or microarray).

A modified substrate or other system for capture of readout gene transcripts or readout proteins may also be included in the kits of the invention, particularly when the kit is designed for use in an array format assay.

In certain embodiments, kits according to the invention include the probes/reagents in the form of an array. The array includes at least two different probes/reagents specific for a readout gene/protein (each probe/reagent specific for a different readout gene/protein) bound to a substrate in a pre-determined pattern (e.g., a grid). The localization of the different probes/reagents allows measurement of levels of a number of different readout genes/proteins in the same reaction.

The instructions relating to the use of the kit for carrying out the invention generally describe how the contents of the kit are used to carry out the methods of the invention. Instructions may include information as sample requirements (e.g., form, pre-assay processing, and size), steps necessary to measure the readout gene(s), and interpretation of results.

Instructions supplied in the kits of the invention are typically written instructions on a label or package insert (e.g., a paper sheet included in the kit), but machine-readable instructions (e.g., instructions carried on a magnetic or optical storage disk) are also acceptable. In certain embodiments, machine-readable instructions comprise software for a programmable digital computer for comparing the measured values obtained using the reagents included in the kit.

Sequence "identity" and "homology", as referred to herein, can be determined using BLAST (Altschul, et al., 1990, *J. Mol. Biol.* 215(3): 403-410), particularly BLASTP 2 as implemented by the National Center for Biotechnology Information (NCBI), using default parameters (e.g., Matrix 0 BLOSUM62, gap open and extension penalties of 11 and 1, respectively, gap x_dropoff 50 and wordsize 3). Unless referred to as "consecutive" amino acids, a sequence optionally can contain a reasonable number of gaps or insertions that improve alignment.

For testing efficacy of an agent believed to alter a stress response, an effective amount of therapeutic agent is administered to a subject having a disease. In some embodiments, the agent is administered at about 0.001 to about 40 milligrams per kilogram total body weight per day (mg/kg/day). In some embodiments the agent is administered at about 0.001 to about 40 mg/kg/day.

The terms "subject" and "individual", as used herein, refer to a vertebrate individual, including avian and mammalian individuals, and more particularly to sport animals (e.g., dogs, cats, and the like), agricultural animals (e.g., cows, horses, sheep, and the like), and primates (e.g., humans).

The term "treatment" is used herein as equivalent to the term "alleviating", which, as used herein, refers to an improvement, lessening, stabilization, or diminution of a symptom of a disease. "Alleviating" also includes slowing or halting progression of a symptom.

For the purposes of this invention, a "clinically useful outcome" refers to a therapeutic or diagnostic outcome that leads to amelioration of the disease condition. "Neuroimmunological stress response" means a disease condition that is characterized by sporadic or episodic elevation of substance P and or calcitonin-related peptide (CGRP) release from sensory nerves into the tissue followed by activation of both inflammatory and anti-inflammatory mechanisms, as well as oxidative damage.

As used herein, "in conjunction with", "concurrent", or "concurrently", as used interchangeably herein, refers to administration of one treatment modality in addition to another treatment modality. As such, "in conjunction with" refers to administration of one treatment modality before, during or after delivery of the other treatment modality to the subject.

Techniques for the manipulation of recombinant DNA are well known in the art, as are techniques for recombinant production of proteins (see, for example, in Sambrook et al., Molecular Cloning: A Laboratory Manual, Vols. 1-3 (Cold Spring Harbor Laboratory Press, 2 ed., (1989); or F. Ausubel et al., Current Protocols in Molecular Biology (Green Publishing and Wiley-Interscience: New York, 1987) and periodic updates). Derivative peptides or small molecules of known composition may also be produced by chemical synthesis using methods well known in the art.

Homologous sequences are orthologous if they were separated by a speciation event: when a species diverges into two separate species, the divergent copies of a single gene in the resulting species are said to be orthologous. Orthologs, or orthologous genes, are genes in different species that are similar to each other because they originated from a common ancestor.

Homologous sequences are paralogous if they were separated by a gene duplication event: if a gene in an organism is duplicated to occupy two different positions in the same genome, then the two copies are paralogous. A set of sequences that are paralogous are called paralogs of each other. Paralogs typically have the same or similar function, but sometimes do not: due to lack of the original selective pressure upon one copy of the duplicated gene, this copy is free to mutate and acquire new functions.

Therapeutic agents are preferably administered via oral or parenteral administration, including but not limited to intravenous (IV), intra-arterial (IA), intraperitoneal (IP), intramuscular (IM), intracardial, subcutaneous (SC), intrathoracic, intraspinal, intradermal (ID), transdermal, oral, sublingual, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The agent may also be delivered in a slow release formulation adapted for IV, IP, IM, ID or SC administration. Inhaled agent is preferably delivered in discrete doses (e.g., via a metered dose inhaler adapted for protein delivery). Administration of a molecule comprising an agent via the transdermal route may be continuous or pulsatile. Administration of agents may also occur orally.

For parenteral administration, compositions comprising a therapeutic agent may be in dry powder, semi-solid or liquid formulations. For parenteral administration by routes other than inhalation, the composition comprising an agent is preferably administered in a liquid formulation. Compositions comprising an agent formulation may contain additional components such as salts, buffers, bulking agents, osmolytes, antioxidants, detergents, surfactants, and other pharmaceutical excipients as are known in the art.

A composition comprising an agent is administered to subjects at a dose of about 0.001 to about 40 mg/kg/day, more preferably about 0.01 to about 10 mg/kg/day, more preferably 0.05 to about 4 mg/kg/day, even more preferably about 0.1 to about 1 mg/kg/day.

As will be understood by those of skill in the art, the symptoms of disease alleviated by the instant methods, as well as the methods used to measure the symptom(s) will vary, depending on the particular disease and the individual patient.

Patients treated in accordance with the methods of the instant invention may experience alleviation of any of the symptoms of their disease.

EXAMPLES

Example 1. Rat Burn Model

The objective of the rat burn experiments was to test the effect of treatment with nephrilin on the neuroimmunological sequelae of burn trauma. The protocol was as follows:

TABLE 1

Drugs and Treatment

| Gr. | N | Agent | mg/kg | Rte | Schedule | days |
|---|---|---|---|---|---|---|
| 1 | 5 | sham | — | sc | daily | 1 |
| 2 | 5 | saline | — | sc | daily | 1 |
| 3 | 5 | nephrilin | 4 | sc | daily | 1 |
| 4 | 5 | sham | — | sc | daily | 14 |
| 5 | 5 | saline | — | sc | daily | 14 |
| 6 | 5 | nephrilin | 4 | sc | daily | 14 |

Burn model protocol: The rat scald burn model (Herndon D N, 1978) induces inflammation and hypermetabolism similar to what is experienced by severely burned people. The rat scald burn model that induces inflammation and hypermetabolism in line with what patients experience is a modified Walker-Mason model. Dr. David Herndon refined this model and has >30 years of experience using this model. This injury, when performed correctly, has a mortality rate of <5%. All animals continue to receive Ensure and water ad libitum throughout the study. Prophylactic analgesia (0.05 mg/kg body weight Buprenorphin) is administered followed by general anesthesia (50 mg/kg body weight Pentobarbital). The dorsum of the trunk and the abdomen are shaved, and a 60% of total body surface area (TBSA) burn administered by placing the animals in a mold exposing defined areas of the skin of the back and abdomen. The mold is placed in 97-99° C. water, the back scalded for 10 seconds and the abdomen for 2 seconds; this method delivers a full-thickness cutaneous burn as confirmed by histologic examination. Burned rats will be resuscitated with 40 cc/kg Ringer's Lactate injected intraperitoneally. Animals are monitored and receive oxygen during the post-burn period until they wake up, at which point they are transferred to their own cages and supervised for another 3-5 hours. If the animals demonstrate discomfort (mobility, loss of appetite, lethargic, fur changes) they are given an analgesic (0.05 mg of buprenorphine). Rounds are conducted twice daily by the investigators and twice daily by the veterinary staff to ensure that animals are comfortable. If the animals demonstrate discomfort (mobility, loss of appetite, lethargic, fur changes) they are given an analgesic (0.05 mg of buprenorphine). Combined observations of movement, eating, drinking, and response to stimuli are used to evaluate the rats, and significant decrease in or cessation of these behaviors are considered evidence of morbidity. Animals meeting these criteria are humanely euthanized. At the end of the study period the animals are first anesthetized with an overdose of Pentobarbital injected intraperitoneally. Once the rats are anesthetized cervical dislocation is performed in a manner consistent with the recommendations of the IACUC, the NIH's Office of Laboratory Animal Welfare (OLAW), and the AVMA. This animal protocol has been approved by the Institutional Animal Care and Use Committee of the University of Texas Medical Branch (see Appendix). The effects of a burn injury on nephrilin were evaluated using ANOVA. Statistical significance was accepted at $p<0.05$. Markers were measured using ELISA. Frozen kidney slices were used for protein and DNA extraction. Differences between treatment groups were evaluated using Student's t-test ($p<0.05$) for comparing effects on plasma and tissue markers.

Figure 1:
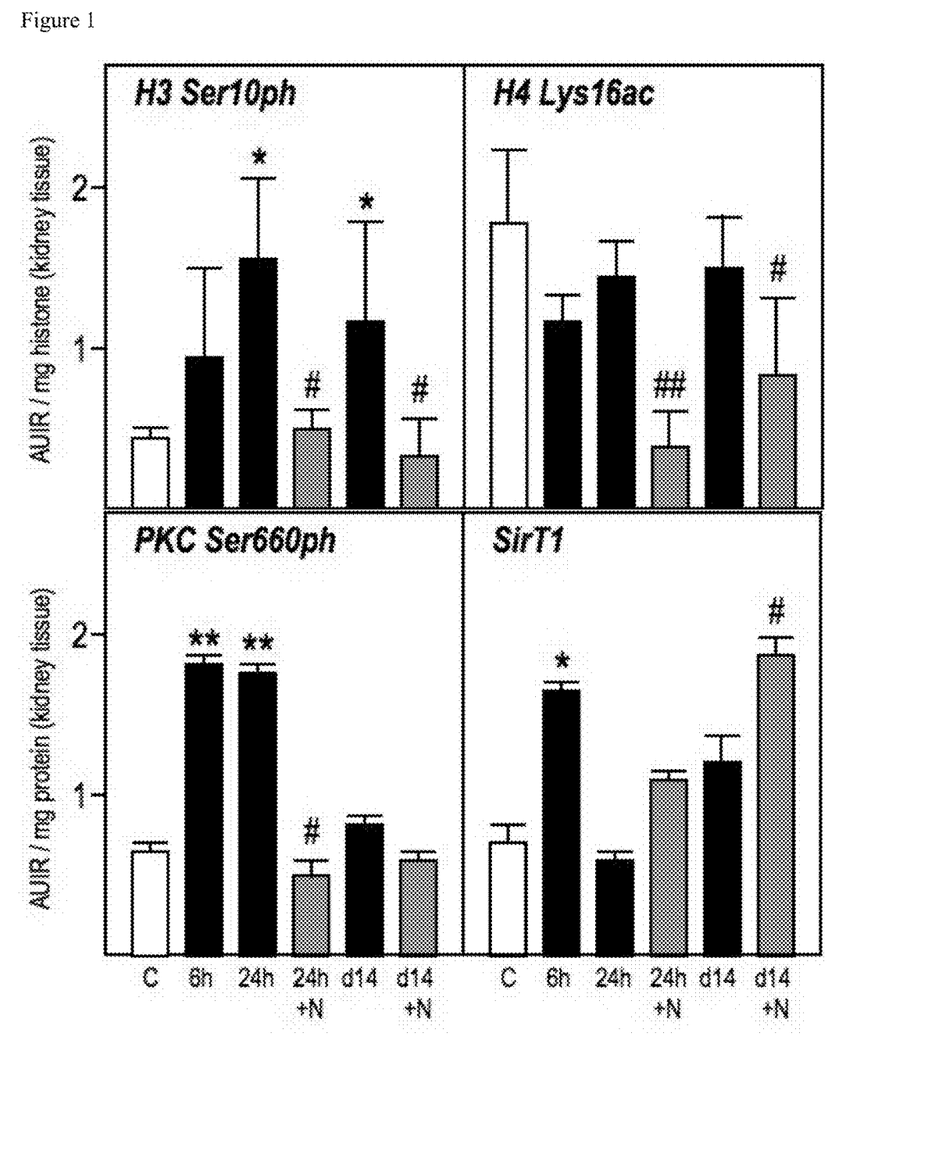
FIG. 1 shows the effect of treatment with nephrilin in a rat burn model. Epigenetic histone modifications in kidney. Open bars=sham, Black bars=burn+saline, Grey bars=burn+nephrilin 4 mg/kg; *p<0.05 and **p<0.01 vs control; #p<0.05 and ##p<0.01 vs burn+saline.
Figure 2:
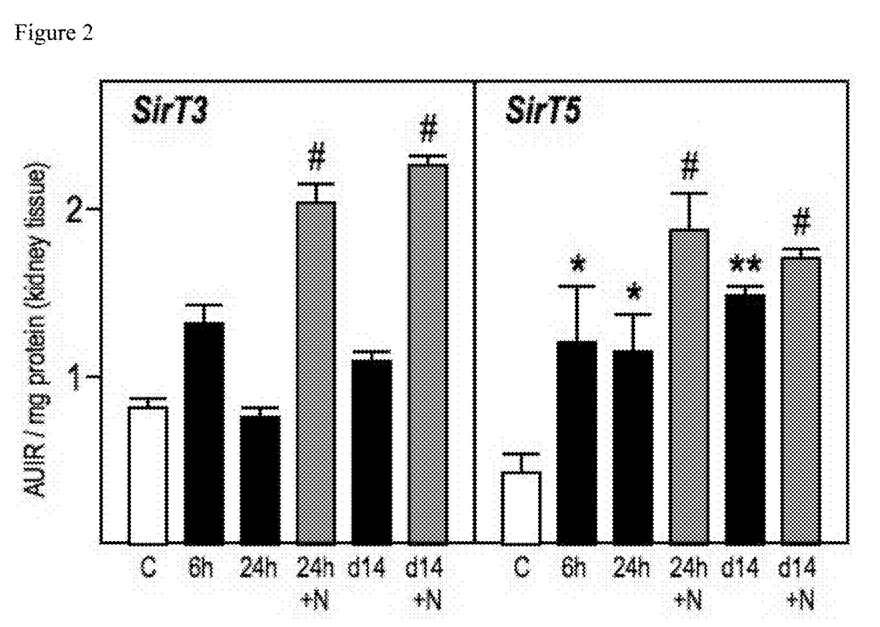
FIG. 2 shows the effect of treatment with nephrilin in a rat burn model. Mitochondrial sirtuins in kidney. Open bars=sham, Black bars=burn+saline, Grey bars=burn+nephrilin 4 mg/kg; *p<0.05 and **p<0.01 vs control; #p<0.05 and ##p<0.01 vs burn+saline.
Figure 3:
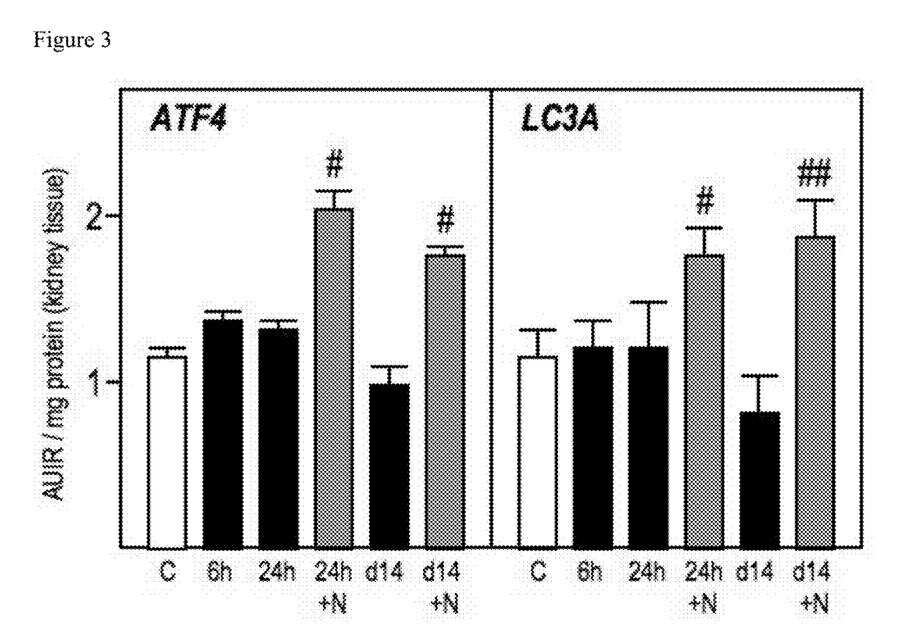
FIG. 3 shows the effect of treatment with nephrilin in a rat burn model. Markers of ER stress and autophagy in kidney. Open bars=sham, Black bars=burn+saline, Grey bars=burn+nephrilin 4 mg/kg; *p<0.05 and **p<0.01 vs control; #p<0.05 and ##p<0.01 vs burn+saline.

Results are shown in FIGS. 1, 2 and 3. Nephrilin treatment significantly modulates epigenetic, mitochondrial and ER stress/autophagy markers in response to burn trauma.

Example 2. Murine Sepsis Models: Cecal Ligation (CLP) and Burn Sepsis Model

The objective of the experiments was to determine sepsis mortality in untreated and nephrilin-treated animals.

TABLE 2

Drugs and Treatment:

| | | 1 Drug/Testing Agent | | | |
|---|---|---|---|---|---|
| Gr. | N | Agent | mg/kg | Route | Comments |
| 1# | 6 | CLP + Saline | — | sc | tail bleed 24 hrs |
| 2 | 6 | CLP + Nephrilin | 4 | sc | " |
| 3 | 4 | Sham | — | — | " |

Control Group

Male C57BL/6 mice used for this study were commercially obtained (Taconic Labs) and were between 8-12 weeks of age. Mice were acclimated to housing suite for one week prior to experiment and had access to food and water ad lib and were on a 12:12 L/D lighting cycle. Mice were anesthetized using 5% vaporized isoflurane. The abdomen was shaved and disinfected prior to surgery. A lateral incision was made through two layers and the cecum exposed and ligated at 0.75 cm from the most distal region of the cecum. Two perforations were made side by side, with a 21.5 gauge needle. After perforation, the ligated portion of the cecum was gently squeezed to expose a small amount of fecal matter. Cecum was returned to the abdominal cavity and abdomen was closed in two layers, using 4-0 braided silk sutures to close the inner peritoneal cavity and 7 mm stainless steel wound clips to close the outer skin layer. Two sham mice were operated on in the same manner, exposing the cecum but no ligation or perforation was made. Before the animal was fully aroused post surgery, 1 mL of 37° C. pre-warmed sterile saline solutions was injected subcutaneously on the animals' dorsal side. Upon arousal, each animal was given a subcutaneous injection of the analgesic, buprenorphine, at 0.05 mg/kg of body weight. Mice were randomly selected to be given either of two treatments, Nephrilin given at a dose of 4 mg/kg of body weight vs. sterile saline solution. Treatments were delivered to mice subcutaneously daily by user blind to treatment identity. 24 hours post-op, blood was collected from each animal. Collection was made from the tail vein into a capillary blood collection tube, coated with EDTA. Blood was also collected at the time of death via cardiac puncture, with the exception of mice found dead over night, where blood collection was not possible. Plasma separation was done in a centrifuge at 700 rpm for 25 mins and immediately stored at −80° C. One kidney was collected per animal at the time of death and immediately stored at −80° C.

TABLE 3

Drugs and Treatment:

| | | 1 Drug/Testing Agent | | | |
|---|---|---|---|---|---|
| Gr. | N | Agent | mg/kg | Route | Comments |
| 1# | 6 | Burn + Control | — | sc | Scrambled sequence |
| 2 | 6 | Burn + Nephrilin | 4 | sc | |

Control Group

Thermally injured mice were created according to a previously reported protocol, as in Example 1. Thus, BALB/c mice (7- to 11-wk-old male, The Jackson Laboratory) were anesthetized with pentobarbital (40 mg/kg, i.p.) and electric clippers were used to shave the hair on the back of each mouse from groin to axilla. A custom made insulated mold (with a 4×5-cm window) was firmly pressed against the shaved backs of the mice. Then, the mice were exposed to a gas flame for 9 seconds. A Bunsen burner equipped with a flame-dispersing cap was used as the source of the gas flame. This procedure consistently produced a third degree burn on approximately 25% of the total body surface area (TBSA) for a 26 g mouse. Immediately after the thermal injury, physiological saline (1 ml per mouse, i.p.) was administered for fluid resuscitation. Along with fluid resuscitation, deaths of mice with 25% TBSA flame burn were not demonstrated within 10 days of burn injury. Control mice had their back hair shaved but were not exposed to the gas flame. They also received physiological saline (1 ml per mouse, i.p.) under the same conditions. To minimize pain and distress, burned mice were treated with buprenorphine (2 mg/kg, s.c.) every 12 h during the postburn period. Sham burn animals (unburned mice) also received identical regimens of analgesics (buprenorphine) throughout the study period. Nephrilin or control peptide at a dose of 4 mg/kg was administered s.c to mice once a day beginning 2 days before burn injury. MRSA (BAA-44 strain), purchased from the American Type Culture Collection, was utilized throughout the study. MRSA was grown in tryptic soy broth for 16 h at 37° C. Two days after the burn injury, mice were infected i.v. with 2×10⁶ CFU/mouse of MRSA (corresponds to 5 $LD_{50}$ in burn mice and <0.1 $LD_{50}$ in unburned mice). The severity of MRSA infection in the test group of mice was determined by their mortality rates, as compared with the control group. To determine the percentage of survival, mice exposed to MRSA were monitored twice a day for 10 days after infection.

Figure 4:
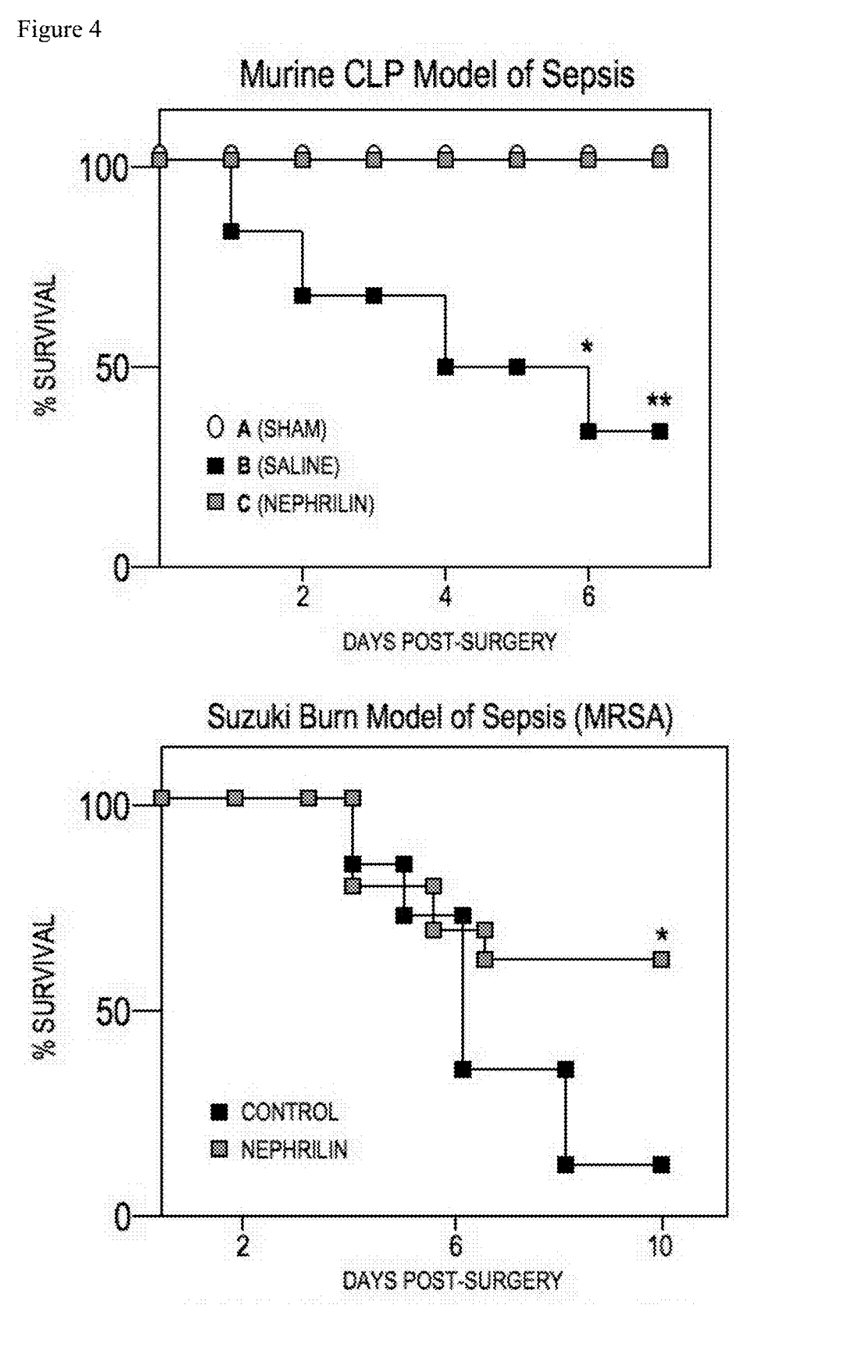
FIG. 4 shows the effect on survival of daily treatment with nephrilin in two murine sepsis models: CLP sepsis model and burn sepsis model.
Figure 5:
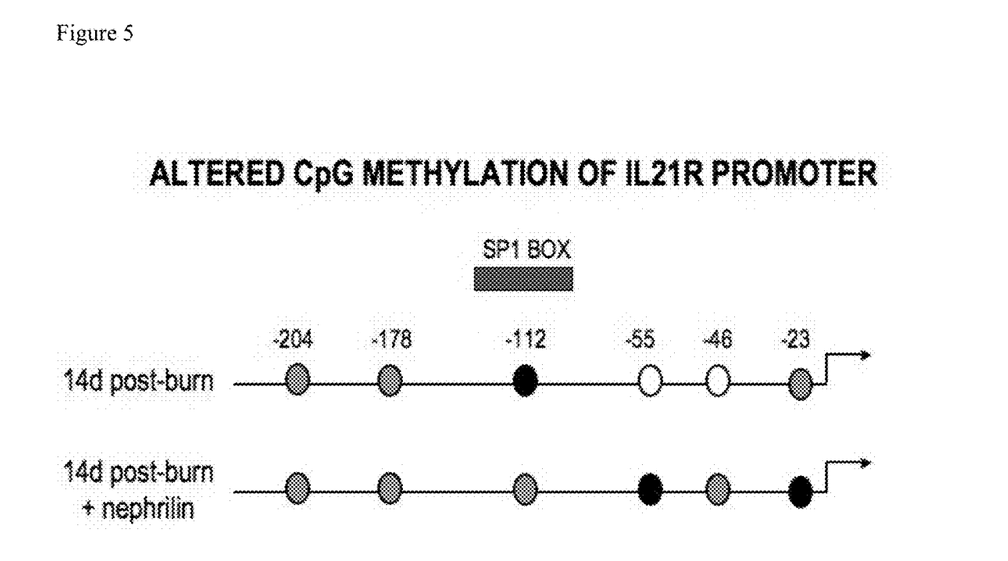
FIG. 5 shows the effect of treatment with nephrilin in a rat burn model. Methylation of promoter region of IL21 receptor gene. CpG methylation at sites numbered relative to start of transcription. Dark ovals=heavily methylated; grey ovals=partially methylated; white ovals=unmethylated. The SP1 box overlaps the CpG at −112.

Tissues were extracted and assayed by ELISA as previously described [Singh B K et al (2010) *Metab Syndr Relat Disord.* 8(4): 355-363]. The results are shown in FIG. 4. They show that nephrilin significantly inhibits mortality in both sepsis models.

Example 3. Timing of Treatment in Herndon Rat Scald Model

Animals were burned as described in Example 1. Animals were injected either with saline or nephrilin beginning two hours after burn (4 mg/kg/day injected subcutaneously once daily for 7 days). Nephrilin treatment was either on days 1-7 or days 8-14. All animals were sacrificed at Day 14. Table 4 shows the results obtained in various analyses of tissues:

TABLE 4

Analysis of rat tissues

| Parameter Measured | Sham (n = 5) | Burn + Saline (n = 8) | Burn + Nephrilin Days 1-7 (n = 8) | Burn + Nephrilin Days 8-14 (n = 5) |
|---|---|---|---|---|
| Glucose (% basal @ t60') | 99.4 ± 1.1 | 118.2 ± 11.1# | 106.8 ± 5.7* | 115.8 ± 6.1 |
| Serum Insulin (pg/ml) | 454 ± 201 | 1114 ± 6443# | 495 ± 362* | 1548 ± 915 |
| Urinary 8-OHDG (ng/pg CysC) | 226 ± 149 | 372 ± 291 | 102 ± 45 | 251 ± 258 |
| Urinary 8-isoprostane (ng/pg CysC) | 8.4 ± 8.5 | 17.3 ± 11.9 | 6.6 ± 4.2 | 14.0 ± 15.5 |
| Kidney p66shc-S36 (phos) AU/mg protein | 9.6 ± 2.8 | 16.2 ± 3.9# | 10.4 ± 2.8* | 13.0 ± 5.5 |
| Kidney pRac1-S71 (phos) AU/mg protein | 6.7 ± 3.7 | 12.3 ± 3.8# | 8.1 ± 1.9* | 11.7 ± 5.9 |
| PKC-beta gene expression** (fold/corrected for GAPDH) | 1.00 | 1.77 | 1.78 | 1.86 |
| Bik gene expression** (fold/corrected for GAPDH) | 1.00 | 3.04 | 2.79 | 2.80 |
| Prex1 gene expression** (fold/corrected for GAPDH) | 1.00 | 2.01 | 1.71 | 1.69 |
| Spleen wt (% body wt) | 0.20 ± 0.05 | 0.46 ± 0.18# | 0.34 ± 0.08 | 0.39 ± 0.19 |

$p < 0.05$ vs sham;
*$p < 0.05$ vs Burn-Saline;
AU = arbitrary units;
**qPCR using total RNA Although the foregoing invention has been described in some detail by way of illustration and example for purposes of clarity of understanding, the descriptions and examples should not be construed as limiting the scope of the invention.

---

What is claimed is:

1. A method for measuring and treating epigenetic oxidative stress response in a mammal, comprising
   (a) obtaining or having obtained a sample of body fluid from the mammal;
   (b) measuring the level of a marker of oxidative stress in said body fluid;
   (c) administering to the mammal a therapeutically effective dose of nephrilin peptide (SEQ ID NO: 1);
   (d) demonstrating
      [i] a reduction in the level of said marker of oxidative stress; and
      [ii] improvement of one or more clinically relevant parameters selected from the group consisting of glycemic control, eGFR, lean body mass, fat mass or wound healing in the mammal;
   thereby mitigating the effects of the epigenetic oxidative stress response in the mammal.

2. The method of claim 1 wherein the epigenetic oxidative stress response is characterized by an increase in H3S10 phosphorylation and/or H3K9/K14 acetylation.

3. The method of claim 1, wherein the stress insult is burn injury.

4. The method of claim 1 wherein the marker of oxidative stress is 8-isoprostane.

5. The method of claim 1, wherein the clinically relevant parameter is glycemic control.

6. The method of claim 1, wherein the clinically relevant parameter is eGFR.

7. The method of claim 1, wherein the clinically relevant parameter is lean body mass.

8. The method of claim 1, wherein the clinically relevant parameter is fat mass.

9. The method of claim 1, wherein the clinically relevant parameter is wound healing.

10. The method of claim 1, wherein the therapeutically effective dose of nephrilin peptide is from about 0.01 mg/kg/day to about 10 mg/kg/day.

11. The method of claim 1, wherein the body fluid is blood or urine.

* * * * *